(12) United States Patent
Müller et al.

(10) Patent No.: US 6,566,536 B2
(45) Date of Patent: May 20, 2003

(54) THIENYLSULPHONYLAMINO(THIO) CARBONYL COMPOUNDS

(75) Inventors: Klaus-Helmut Müller, Düsseldorf (DE); Ernst Rudolf F. Gesing, Erkrath (DE); Mark Wilhelm Drewes, Langenfeld (DE); Johannes Rudolf Jansen, Monheim (DE); Rolf Kirsten, Monheim (DE); Joachim Kluth, Langenfeld (DE); Klaus König, Odenthal (DE); Ulrich Philipp, Köln (DE); Markus Dollinger, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/014,967

(22) Filed: Nov. 9, 2001

(65) Prior Publication Data

US 2003/0004354 A1 Jan. 2, 2003

Related U.S. Application Data

(62) Division of application No. 09/319,021, filed as application No. PCT/EP97/06560 on Nov. 24, 1997, now Pat. No. 6,383,988.

(30) Foreign Application Priority Data

Dec. 4, 1996 (DE) .......................... 196 50 196

(51) Int. Cl.⁷ ............................. C07D 333/34
(52) U.S. Cl. ........................... 549/65; 549/61
(58) Field of Search .................. 549/61, 65

(56) References Cited

U.S. PATENT DOCUMENTS

| | | | |
|---|---|---|---|
| 4,666,502 A | 5/1987 | Seckinger et al. ............. 71/90 |
| 4,877,440 A | 10/1989 | Christensen et al. ........... 71/90 |
| 5,085,684 A | 2/1992 | Muller et al. ................. 71/92 |
| 5,094,683 A | 3/1992 | Daum ........................... 71/94 |
| 5,149,356 A | 9/1992 | Muller et al. ................. 71/90 |
| 5,205,853 A | 4/1993 | Wolf et al. .................. 504/247 |
| 5,238,910 A | 8/1993 | Muller et al. ................ 504/273 |
| 5,241,074 A | 8/1993 | Daum et al. ................. 548/263.8 |
| 5,252,540 A | 10/1993 | Heistracher et al. ......... 504/280 |
| 5,276,162 A | 1/1994 | Muller et al. ............... 548/263.4 |
| 5,300,480 A | 4/1994 | Haas et al. .................. 504/273 |
| 5,380,864 A | 1/1995 | Muller et al. ............... 548/263.8 |
| 5,405,970 A | 4/1995 | Daum et al. ................. 548/263.6 |
| 5,488,028 A | 1/1996 | Haas et al. |
| 5,532,378 A | 7/1996 | Daum et al. ................. 548/263.8 |
| 5,534,486 A | 7/1996 | Muller et al. ................ 504/273 |
| 5,541,337 A | 7/1996 | Müller et al. ............... 548/263.6 |
| 5,554,761 A | 9/1996 | Haas et al. ................. 548/263.6 |
| 5,597,939 A | 1/1997 | Muller et al. .................. 558/8 |
| 5,599,944 A | 2/1997 | Muller et al. ............... 548/262.6 |
| 5,625,074 A | 4/1997 | Daum et al. ................. 548/263.8 |
| 5,631,380 A | 5/1997 | Haas et al. ................. 548/263.4 |
| 5,652,372 A | 7/1997 | Muller et al. ............... 548/263.4 |
| 5,750,718 A | 5/1998 | Muller et al. ............... 548/263.6 |

FOREIGN PATENT DOCUMENTS

| DE | 195 40 737 | 5/1997 |
|---|---|---|
| EP | 0 207 609 | 1/1992 |

*Primary Examiner*—Patricia L. Morris
(74) *Attorney, Agent, or Firm*—Richard E. L. Henderson; Raymond J. Harmuth

(57) ABSTRACT

The invention relates to novel thienylsulphonylamino(thio) carbonyl compounds of the formula (I),

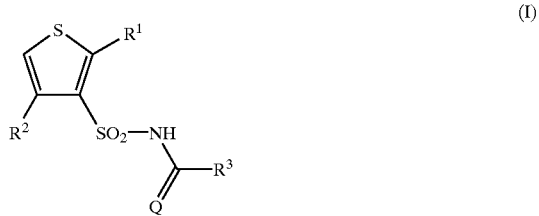

in which
  Q represents oxygen or sulphur,
  $R^1$ represents cyano, halogen or in each case optionally cyano-, halogen- or $C_1$–$C_4$-alkoxy-substituted alkyl, alkenyl, alkinyl, alkoxy, alkenyloxy or alkinyloxy having in each case up to 6 carbon atoms,
  $R^2$ represents cyano, halogen or in each case optionally cyano-, halogen- or $C_1$–$C_4$-alkoxy-substituted alkyl, alkenyl, alkinyl, alkoxy, alkenyloxy or alkinyloxy having in each case up to 6 carbon atoms, and
  $R^3$ represents in each case optionally substituted heterocyclyl having 5 ring members, at least one of which represents oxygen, sulphur or nitrogen and one to three others may represent nitrogen, and salts of compounds of the formula (I), to processes and novel intermediates for preparing the novel compounds and to their use as herbicides.

3 Claims, No Drawings

THIENYLSULPHONYLAMINO(THIO) CARBONYL COMPOUNDS

This Application is a divisional patent application of U.S. patent application Ser. No. 09/319,021 filed Jun. 1, 1999 to Muller et al, which subsequently issued as U.S. Pat. No. 6,383,988 on May 7, 2002, which in turn was the national stage of PCT Application No. PCT/EP97/06560 filed Nov. 24, 1997, which in turn claimed and perfected its claim of priority of German Patent Application No. 196 50 196.2 filed Dec. 4, 1996, priority of which is hereby claimed in the present Application.

The invention relates to novel thienylsulphonylamino (thio)carbonyl compounds, to a plurality of processes and novel intermediates for their preparation and to their use as herbicides.

It is already known that certain sulphonylaminocarbonyl compounds have herbicidal properties (cf. EP 341489, EP 422469, EP 425948, EP 431291, EP 507171, EP 534266, DE 4029753). However, the activity of these compounds is not in all respects satisfactory.

This invention, accordingly, provides the novel thienylsulphonylamino(thio)-carbonyl compounds of the general formula (I),

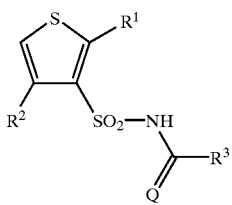

(I)

in which

Q represents oxygen or sulphur, $R^1$ represents cyano, halogen or in each case optionally cyano-, halogen- or $C_1$–$C_4$-alkoxy-substituted alkyl, alkenyl, alkinyl, alkoxy, alkenyloxy or alkinyloxy having in each case up to 6 carbon atoms, $R^2$ represents cyano, halogen or in each case optionally cyano-, halogen- or $C_1$–$C_4$-alkoxy-substituted alkyl, alkenyl, alkinyl, alkoxy, alkenyloxy or alkinyloxy having in each case up to 6 carbon atoms, and $R^3$ represents in each case optionally substituted heterocyclyl having 5 ring members, at least one of which represents oxygen, sulphur or nitrogen and one to three others may represent nitrogen, and salts of compounds of the formula (I).

The novel thienylsulphonylamino(thio)carbonyl compounds of the general formula (I) are obtained when (a) sulphonamides of the general formula (II)

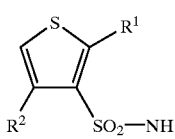

(II)

in which $R^1$ and $R^2$ are each as defined above, are reacted with (thio)carboxylic acid derivatives of the general formula (III)

(III)

in which

Q and $R^3$ are each as defined above and

Z represents halogen, alkoxy, aryloxy or arylalkoxy, if appropriate in the presence of an acid acceptor and if appropriate in the presence of a diluent, or when (b) sulphonyl iso(thio)cyanates of the general formula (IV)

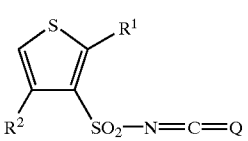

(IV)

in which

Q, $R^1$ and $R^2$ are each as defined above, are reacted with heterocycles of the general formula (V)

(V)

in which $R^{3-1}$ represents optionally substituted heterocyclyl having 5 ring members, at least one of which represents >N—H, if appropriate in the presence of a reaction auxiliary and if appropriate in the presence of a diluent, or when (c) sulphonyl chlorides of the general formula (VI)

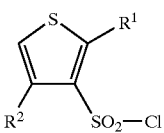

(VI)

in which $R^1$ and $R^2$ are each as defined above, are reacted with heterocycles of the general formula (V)

(V)

in which $R^{3-1}$ is as defined above under (b), and metal (thio)cyanates of the general formula (VII)

(VII)

in which

Q is as defined above and

M represents a metal equivalent, if appropriate in the presence of a reaction auxiliary and if appropriate in the presence of a diluent, or when (d) sulphonyl chlorides of the general formula (VI)

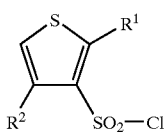

(VI)

in which
R¹ and R² are each as defined above,
are reacted with (thio)carboxamides of the general formula (VIII)

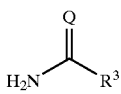

(VIII)

in which
Q and R³ are each as defined above under formula (I),
if appropriate in the presence of an acid acceptor and if appropriate in the presence of a diluent,
or when
(e) sulphonylamino(thio)carbonyl compounds of the general formula (IX)

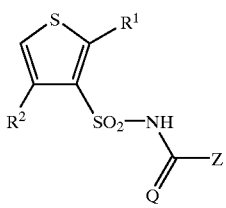

(IX)

in which
Q, R¹ and R² are each as defined above and
Z represents halogen, alkoxy, aryloxy or arylalkoxy,
are reacted with heterocycles of the general formula (V)

 (V)

in which
$R^{3-1}$ is as defined above under (b),
if appropriate in the presence of an acid acceptor and if appropriate in the presence of a diluent,
and the compounds of the formula (I) obtained by the processes (a), (b), (c), (d) or (e) are, if appropriate, converted into salts by customary methods.

According to their nature, the processes (b), (c) and (e) are only suitable for preparing those compounds of the formula (I) in which $R^3$ represents $R^{3-1}$.

The novel thienylsulphonylamino(thio)carbonyl compounds of the general formula (I) have strong herbicidal activity.

The invention preferably provides compounds of the formula (I) in which

Q represents oxygen or sulphur, $R^1$ represents cyano, halogen, represents optionally cyano-, halogen- or $C_1$–$C_4$-alkoxy-substituted $C_1$–$C_4$-alkyl, represents in each case optionally cyano- or halogen-substituted $C_2$–$C_4$-alkenyl or $C_2$–$C_4$-alkinyl, represents optionally cyano-, halogen- or $C_1$–$C_4$-alkoxy-substituted $C_1$–$C_4$-alkoxy, or represents in each case optionally cyano- or halogen-substituted $C_2$–$C_4$-alkenyloxy or $C_2$–$C_4$-alkinyloxy, $R^2$ represents cyano, halogen, represents optionally cyano-, halogen- or $C_1$–$C_4$-alkoxy-substituted $C_1$–$C_4$-alkyl, represents in each case optionally cyano- or halogen-substituted $C_2$–$C_4$-alkenyl or $C_2$–$C_4$-alkinyl, represents optionally cyano-, halogen- or $C_1$–$C_4$-alkoxy-substituted $C_1$–$C_4$-alkoxy, or represents in each case optionally cyano- or halogen-substituted $C_2$–$C_4$-alkenyloxy or $C_2$–$C_4$-alkinyloxy, and $R^3$ represents in each case optionally substituted heterocyclyl of the formulae below

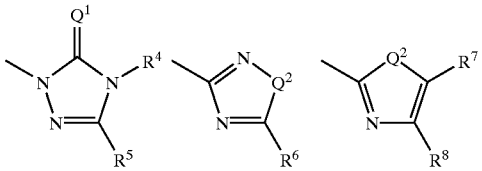

in which
$Q^1$, $Q^2$ and $Q^3$ each represent oxygen or sulphur and
$R^4$ represents hydrogen, hydroxyl, amino, cyano, represents $C_2$–$C_{10}$-alkylideneamino, represents optionally fluorine-, chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, represents in each case optionally fluorine-, chlorine- and/or bromine-substituted $C_2$–$C_6$-alkenyl or $C_2$–$C_6$-alkinyl, represents in each case optionally fluorine-, chlorine-, bromine-, cyano-, $C_1$–$C_4$-alkoxy- or $C_1$–$C_4$-alkoxy-carbonyl-substituted $C_1$–$C_6$-alkoxy, $C_1$–$C_6$-alkylamino or $C_1$–$C_6$-alkyl-carbonylamino, represents $C_3$–$C_6$-alkenyloxy, represents di-($C_1$–$C_4$-alkyl)-amino, represents in each case optionally fluorine-, chlorine-, bromine-, cyano- and/or $C_1$–$C_4$-alkyl-substituted $C_3$–$C_6$-cycloalkyl, $C_3$–$C_6$-cycloalkylamino or $C_3$–$C_6$-cycloalkyl-$C_1$–$C_4$-alkyl, or represents in each case optionally fluorine-, chlorine-, bromine-, cyano-, nitro-, $C_1$–$C_4$-alkyl-, trifluoromethyl and/or $C_1$–$C_4$-alkoxy-substituted phenyl or phenyl-$C_1$–$C_4$-alkyl, $R^5$ represents hydrogen, hydroxyl, mercapto, amino, cyano, fluorine, chlorine, bromine, iodine, represents optionally fluorine-, chlorine-, bromine-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, represents in each case optionally fluorine-, chlorine- and/or bromine-substituted $C_2$–$C_6$-alkenyl or $C_2$–$C_6$-alkinyl, represents in each case optionally fluorine-, chlorine-, cyano-, $C_1$–$C_4$-alkoxy- or $C_1$–$C_4$-alkoxy-carbonyl-substituted $C_1$–$C_6$-alkoxy, $C_1$–$C_6$-alkylthio, $C_1$–$C_6$-alkylamino or $C_1$–$C_6$-alkyl-carbonylamino, represents $C_3$–$C_6$-alkenyloxy, $C_3$–$C_6$-alkinyloxy, $C_3$–$C_6$-alkenylthio, $C_3$–$C_6$-alkinylthio, $C_3$–$C_6$-alkenylamino or $C_3$–$C_6$-alkinylamino, represents di-($C_1$–$C_4$-alkyl)-amino, represents in each case optionally methyl- and/or ethyl-substituted aziridino, pyrrolidino, piperidino or morpholino, represents in each case optionally fluorine-, chlorine-, bromine-, cyano -and/or $C_1$–$C_4$-alkyl-substituted $C_3$–$C_6$-cycloalkyl, $C_5$–$C_6$-cycloalkenyl, $C_3$–$C_6$-cycloalkyloxy, $C_3$–$C_6$-cycloalkylthio, $C_3$–$C_6$-cycloalkylamino, $C_3$–$C_6$-cycloalkyl-$C_1$–$C_4$-alkyl, $C_3$–$C_6$-cycloalkyl-$C_1$–$C_4$-alkoxy, $C_3$–$C_6$-cycloalkyl-$C_1$–$C_4$-alkylthio or $C_3$–$C_6$-cycloalkyl-$C_1$–$C_4$-alkylamino, or represents in each case optionally fluorine-, chlorine-, bromine-, cyano-, nitro-, $C_1$–$C_4$-alkyl-, trifluoromethyl-, $C_1$–$C_4$-alkoxy- and/or $C_1$–$C_4$-alkoxy-carbonyl-substituted phenyl, phenyl-$C_1$–$C_4$-alkyl, phenoxy, phenyl-$C_1$–$C_4$-alkoxy, phenylthio, phenyl-$C_1$–$C_4$-alkylthio, phenylamino or phenyl-$C_1$–$C_4$-alkylamino, or $R^4$ and $R^5$ together represent optionally branched alkanediyl having 3 to 11 carbon atoms, futhermore $R^6$, $R^7$ and $R^8$ are identical or different and each represent hydrogen, cyano, fluorine, chlorine, bromine, or represent in each case optionally fluorine-, chlorine-, bromine- or $C_1$–$C_4$-alkoxy-substituted alkyl, alkenyl, alkinyl, alkoxy, alkenyloxy, alkinyloxy, alkylthio, alkenylthio, alkinylthio, alkylsulphinyl or alkylsulphonyl having in each case up to 6 carbon atoms or represent optionally cyano-, fluorine-, chlorine-, bromine or $C_1$–$C_4$-alkyl-substituted cycloalkyl having 3 to 6 carbon atoms.

The invention furthermore preferably provides sodium, potassium, magnesium, calcium ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$- or $C_6$-cycloalkyl-ammonium and di-($C_1$–$C_2$-alkyl)-benzyl-ammonium salts of compounds of the formula (I) in which Q, $R^1$, $R^2$ and $R^3$ each have the meaning given above as being preferred.

The invention in particular provides compounds of the formula (I) in which

Q represents oxygen or sulphur, $R^1$ represents cyano, fluorine, chlorine, bromine, represents in each case optionally cyano-, fluorine-, chlorine-, methoxy- or ethoxy-substituted methyl, ethyl, n- or i-propyl, n-, i- or s-butyl, represents in each case optionally cyano-, fluorine- or chlorine-substituted propenyl, butenyl, propinyl or butinyl, represents in each case optionally cyano-, fluorine-, chlorine-, methoxy- or ethoxy-substituted methoxy, ethoxy, n- or i-propoxy, n-, i-, s- or t-butoxy, or represents in each case optionally cyano-, fluorine- or chlorine-substituted propenyloxy, butenyloxy, propinyloxy or butinyloxy, $R^2$ represents cyano, fluorine, chlorine, bromine, represents in each case optionally cyano-, fluorine-, chlorine-, methoxy- or ethoxy-substituted methyl, ethyl, n- or i-propyl, n-, i- or s-butyl, represents in each case optionally cyano-, fluorine- or chlorine-substituted propenyl, butenyl, propinyl or butinyl, represents in each case optionally cyano-, fluorine-, chlorine-, methoxy- or ethoxy-substituted methoxy, ethoxy, n- or i-propoxy, n-, i-, s- or t-butoxy, or represents in each case optionally cyano-, fluorine- or chlorine-substituted propenyloxy, butenyloxy, propinyloxy or butinyloxy, and $R^3$ represents in each case optionally substituted heterocyclyl of the formulae below

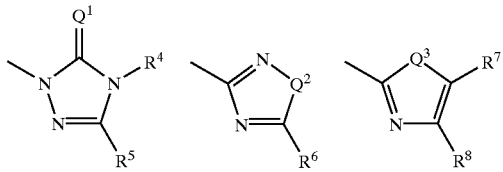

in which $Q^1$, $Q^2$ and $Q^3$ each represent oxygen or sulphur and $R^4$ represents hydrogen, hydroxyl, amino, represents in each case optionally fluorine-, chlorine-, cyano-, methoxy- or ethoxy-substituted methyl, ethyl, n- or i-propyl, n-, i-, s- or t-butyl, represents in each case optionally fluorine-, chlorine- or bromine-substituted propenyl, butenyl, propinyl or butinyl, represents in each case optionally fluorine-, chlorine-, cyano-, methoxy- or ethoxy-substituted methoxy, ethoxy, n- or i-propoxy, n-, i-, s- or t-butoxy, methylamino, ethylamino, n- or i-propylamino, n-, i-, s- or t-butylamino, represents propenyloxy or butenyloxy, represents dimethylamino or diethylamino, represents in each case optionally fluorine-, chlorine-, methyl- and/or ethyl-substituted cyclopropyl, cyclobutyl, cyclopentyl, cyclohexyl, cyclopropylamino, cyclobutylamino, cyclopentylamino, cyclohexylamino, cyclopropylmethyl, cyclobutylmethyl, cyclopentylmethyl or cyclohexylmethyl, or represents in each case optionally fluorine-, chlorine-, methyl-, trifluoromethyl- and/or methoxy-substituted phenyl or benzyl $R^5$ represents hydrogen, hydroxyl, mercapto, amino, fluorine, chlorine, bromine, represents in each case optionally fluorine-, chlorine-, cyano-, methoxy- or ethoxy-substituted methyl, ethyl, n- or i-propyl, n-, i-, s- or t-butyl, represents in each case optionally fluorine-, chlorine- or bromine-substituted ethenyl, propenyl, butenyl, propinyl or butinyl, represents in each case optionally fluorine-, chlorine-, cyano-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, represents propenyloxy, butenyloxy, propinyloxy, butinyloxy, propenylthio, propadienylthio, butenylthio, propinylthio, butinylthio, propenylamino, butenylamino, propinylamino or butinylamino, represents dimethylamino, diethylamino or dipropylamino, represents in each case optionally fluorine-, chlorine-, methyl- and/or ethyl-substituted cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluorine-, chlorine-, methyl-, trifluoromethyl-, methoxy- and/or methoxycarbonyl-substituted phenyl, benzyl, phenoxy, benzyloxy, phenylthio, benzylthio, phenylamino or benzylamino, or $R^4$ and $R^5$ together represent optionally branched alkanediyl having 3 to 11 carbon atoms, furthermore $R^6$, $R^7$ and $R^8$ are identical or different and each represent hydrogen, cyano, fluorine, chlorine, bromine, or represent in each case optionally fluorine-, chlorine-, methoxy- or ethoxy-substituted methyl, ethyl, n- or i-propyl, n-, i-, s- or t-butyl, propenyl, butenyl, propinyl, butinyl, methoxy, ethoxy, n- or i-propoxy, n-, i-, s- or t-butoxy, propenyloxy, butenyloxy, propinyloxy, butinyloxy, methylthio, ethylthio, n- or i-propylthio, n-, i-, s- or t-butylthio, propenylthio, butenylthio, propinylthio, butinylthio, methylsulphinyl, ethylsulphinyl, methylsulphonyl or ethylsulphonyl, or represent cyclopropyl.

A very particularly preferred group of compounds according to the invention are those compounds of the formula (I) in which Q represents oxygen or sulphur, $R^1$ represents methyl, ethyl, n- or i-propyl, $R^2$ represents methyl, ethyl, n- or i-propyl and $R^3$ represents optionally substituted triazolinyl of the formula below

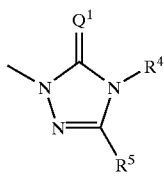

in which

Q¹ represents oxygen or sulphur and

R⁴ represents in each case optionally fluorine-, chlorine-, methoxy- or ethoxy-substituted methyl, ethyl, n- or i-propyl, represents in each case optionally fluorine- or chlorine-substituted propenyl or propinyl, represents methoxy, ethoxy, n- or i-propoxy, methylamino, ethylamino, n- or i-propylamino, represents propenyloxy, represents dimethylamino or represents cyclopropyl, R⁵ represents chlorine or bromine, represents in each case optionally fluorine-, chlorine-, cyano-, methoxy- or ethoxy-substituted methyl, ethyl, n- or i-propyl, n-, i-, s- or t-butyl, represents in each case optionally fluorine-, chlorine- or bromine-substituted ethenyl, propenyl, butenyl, propinyl or butinyl, represents in each case optionally fluorine-, chlorine-, cyano-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, represents propenyloxy, butenyloxy, propinyloxy, butinyloxy, propenylthio, propadienylthio, butenylthio, propinylthio, butinylthio, propenylamino, butenylamino, propinylamino or butinylamino, represents dimethylamino, diethylamino or dipropylamino, represents in each case optionally fluorine-, chlorine-, methyl- and/or ethyl-substituted cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents in each case optionally fluorine-, chlorine-, methyl-, trifluoromethyl-, methoxy- and/or methoxycarbonyl-substituted phenyl, benzyl, phenoxy, benzyloxy, phenylthio, benzylthio, phenylamino or benzylamino, or R⁴ and R⁵ together represent optionally branched alkanediyl having 3 to 11 carbon atoms.

The abovementioned general or preferred radical definitions apply both to the end products of the formula (I) and, correspondingly, to the starting materials or intermediates required in each case for the preparation. These radical definitions can be combined with each other as desired, that is to say combinations between the stated preferred ranges are also possible.

Using, for example, 4-bromo-2-methyl-thiophene-3-sulphonamide and 5-ethoxy-4-methyl-2-phenoxycarbonyl-2,4-dihydro-3H-1,2,4-triazol-3-thione as starting materials, the course of the reaction in the process (a) according to the invention can be illustrated by the following equation:

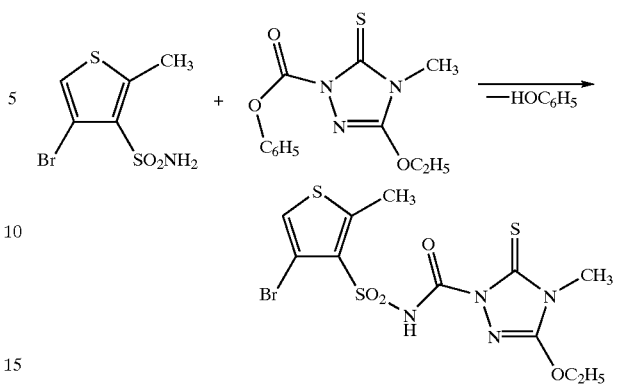

Using, for example, 4-chloro-2-ethyl-3-thienylsulphonyl isothiocyanate and 5-ethyl-4-methoxy-2,4-dihydro-3H-1,2,4-triazol-3-one as starting materials, the course of the reaction in the process (b) according to the invention can be illustrated by the following equation:

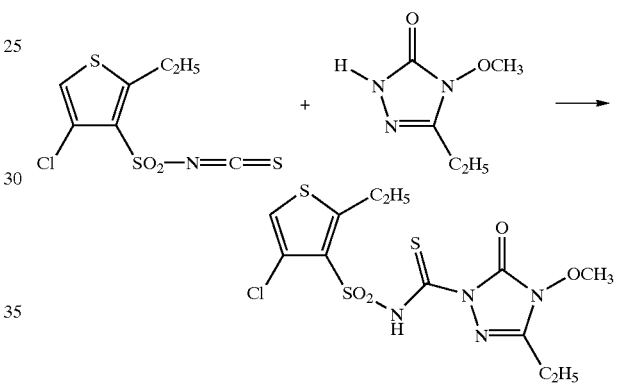

Using, for example, 4-ethyl-2-methoxy-thiophene-3-sulphonyl chloride, 5-ethylthio-4-methoxy-2,4-dihydro-3H-1,2,4-triazol-3-one and potassium cyanate as starting materials, the course of the reaction in the process (c) according to the invention can be illustrated by the following equation:

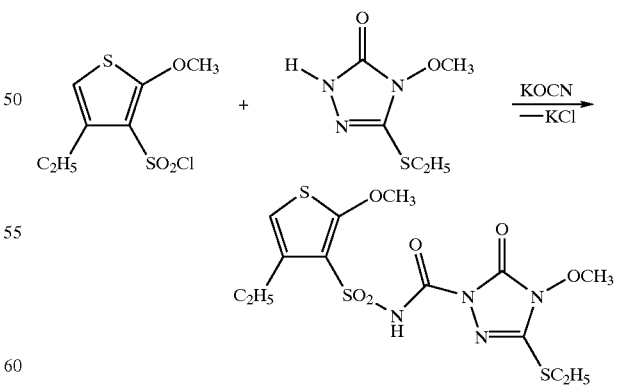

Using for example, 4-cyano-2-isopropyl-thiophene-3-sulphonly chloride and 5-methyl-1,2,4-oxadiazole-3-carboxamide as starting materials, the course of the reaction in the process (d) according to the invention can be illustrated by the following equation:

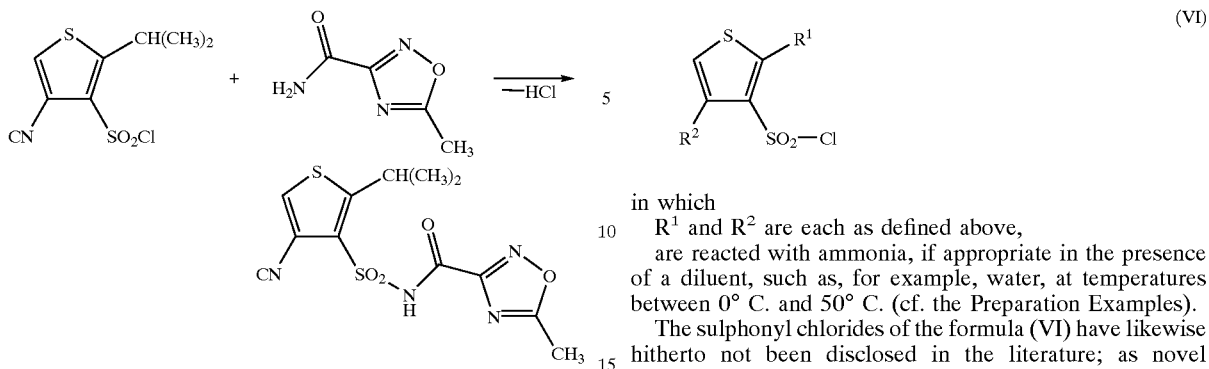

Using, for example, N-(4-fluoro-2-trifluoromethyl-thiophen-3-yl-sulphonyl)-O-methyl-urethane and 4-methyl-5-methylthio-2,4-dihydro-3H-1,2,4-triazol-3-one as starting materials, the course of the reaction in the process (e) according to the invention can be illustrated by the following equation:

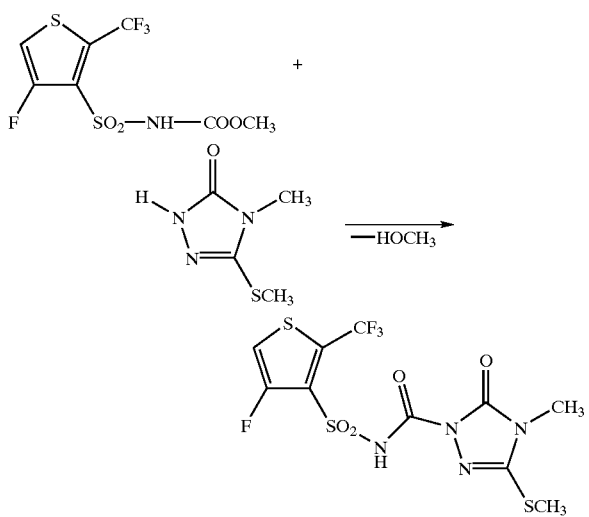

The formula (II) provides a general definition of the sulphonamides to be used as starting materials in the process (a) according to the invention for preparing the compounds of the formula (I). In the formula (II), $R^1$ and $R^2$ each preferably or in particular have those meanings which have already been mentioned above, in the description of the compounds of the formula (I) according to the invention, as being preferred or as being particularly preferred for $R^1$ and $R^2$.

The starting materials of the formula (II) have hitherto not been disclosed in the literature; as novel substances, they also form part of the subject-matter of the present application.

The novel sulphonamides of the formula (II) are obtained when sulphonyl chlorides of the formula (VI)

in which
$R^1$ and $R^2$ are each as defined above,
are reacted with ammonia, if appropriate in the presence of a diluent, such as, for example, water, at temperatures between 0° C. and 50° C. (cf. the Preparation Examples).

The sulphonyl chlorides of the formula (VI) have likewise hitherto not been disclosed in the literature; as novel substances, they also form part of the subject-matter of the present application.

The novel sulphonyl chlorides of the formula (VI) are obtained when corresponding amino compounds of the general formula (X)

(X)

in which
$R^1$ and $R^2$ are each as defined above,
are reacted with an alkali metal nitrite, such as, for example, sodium nitrite, in the presence of hydrochloric acid at temperatures between −10° C. and +10° C. and the resulting diazonium salt solution is reacted with sulphur dioxide in the presence of a diluent, such as, for example, dichloromethane, 1,2-dichloroethane or acetic acid, and in the presence of a catalyst, such as, for example, copper(I) chloride and/or copper(II) chloride, at temperatures between −10° C. and +50° C. (cf. the Preparation Examples).

The amino compounds of the formula (X) required as precursors are known and/or can be prepared by processes known per se (cf. DE 33 03 388).

The formula (III) provides a general definition of the (thio)carboxylic acid derivatives further to be used as starting materials in the process (a) according to the invention for preparing the compounds of the formula (I). In the formula (III), Q and $R^3$ each preferably or in particular have that meaning which has already been mentioned above, in the description of the compounds of the formula (I) according to the invention, as being preferred or as being particularly preferred for Q and $R^3$; Z preferably represents fluorine, chlorine, bromine, $C_1$–$C_4$-alkoxy, phenoxy or benzyloxy, in particular represents chlorine, methoxy, ethoxy or phenoxy.

The starting materials of the formula (III) are known and/or can be prepared by processes known per se (cf. EP 459244, EP 341489, EP 422469, EP 425948, EP 431291, EP 507171, EP 534266).

The formula (IV) provides a general definition of the sulphonyl iso(thio)cyanates to be used as starting materials in the process (b) according to the invention for preparing the compounds of the formula (I). In the formula (IV), Q, $R^1$ and $R^2$ each preferably or in particular have that meaning which has already been mentioned above, in the description of the compounds of the formula (I) according to the invention, as being preferred or as being particularly preferred for Q, $R^1$ and $R^2$.

The sulphonyl iso(thio)cyanates of the formula (IV) have hitherto not been disclosed in the literature; as novel substances, they also form part of the subject-matter of the present application.

The novel sulphonyl iso(thio)cyanates of the formula (IV) are obtained when sulphonamides of the general formula (II)—above—are reacted with phosgene and thiophosgene, respectively, if appropriate in the presence of an alkyl isocyanate, such as, for example, butyl isocyanate, if appropriate in the presence of a reaction auxiliary, such as, for example, diazabicyclo[2.2.2]octane, and in the presence of a diluent, such as, for example, toluene, xylene or chlorobenzene, at temperatures between 80° C. and 150° C. and the volatile components are distilled off under reduced pressure after the reaction has ended (cf. the Preparation Examples).

The formula (V) provides a general definition of the heterocycles to be used as starting materials in the processes (b), (c) and (e) according to the invention. In the formula (V), $R^{3-1}$ preferably represents optionally substituted triazolinyl of the formula below

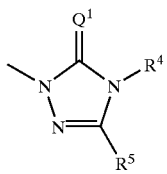

in which $Q^1$ represents oxygen or sulphur and the radicals $R^4$ and $R^5$ each preferably or in particular have those meanings which have already been mentioned above, in the description of the compounds of the formula (I) according to the invention, as being preferred or as being particularly preferred for $R^4$ and $R^5$.

The starting materials of the formula (V) are known and/or can be prepared by processes known per se (cf. EP 341489, EP 422469, EP 425948, EP 431291, EP 507171, EP 534266).

The formula (VI) provides a general definition of the sulphonyl chlorides to be used as starting materials in the processes (c) and (d) according to the invention for preparing the compounds of the formula (I). In the formula (VI), $R^1$ and $R^2$ each preferably or in particular have that meaning which has already been mentioned above, in the description of the compounds of the formula (I) according to the invention, as being preferred or as being particularly preferred for $R^1$ and $R^2$.

The sulphonyl chlorides of the formula (VI) have hitherto not been disclosed in the literature; as novel substances, they also form part of the subject-matter of the present application and they can be prepared as described above.

The formula (VIII) provides a general definition of the (thio)carboxamides to be used as starting materials in the process (d) according to the invention for preparing the compounds of the formula (I). In the formula (VIII), Q and $R^3$ each preferably or in particular have that meaning which has already been mentioned above, in the description of the compounds of the formula (I) according to the invention, as being preferred or as being particularly preferred for Q and $R^3$.

The starting materials of the formula (VIII) are known and/or can be prepared by processes known per se (cf. EP 459244).

The formula (IX) provides a general definition of the sulphonylamino-(thio)carbonyl compounds to be used as starting materials in the process (e) according to the invention for preparing the compounds of the formula (I). In the formula (IX), Q, $R^1$ and $R^2$ each preferably or in particular has that meaning which has already been mentioned above, in the description of the compounds of the formula (I) according to the invention, as being preferred or as being particularly preferred for Q, $R^1$ and $R^2$; Z preferably represents fluorine, chlorine, bromine, $C_1-C_4$-alkoxy, phenoxy or benzyloxy, in particular represents chlorine, methoxy, ethoxy or phenoxy.

The starting materials of the formula (IX) are known and/or can be prepared by processes known per se.

The processes (a), (b), (c), (d) and (e) according to the invention for preparing the novel compounds of the formula (I) are preferably carried out using diluents. Suitable diluents are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene; ethers such as diethyl ether and dibutyl ether, glycol dimethyl ether and diglycol dimethyl ether, tetrahydrofuran and dioxane; ketones such as acetone, methyl ethyl ketone, methyl isopropyl ketone and methyl isobutyl ketone; esters such as methyl acetate and ethyl acetate; nitriles such as, for example, acetonitrile and propionitrile; amides such as, for example, dimethylformamide, dimethylacetamide and N-methylpyrrolidone and also dimethyl sulphoxide, tetramethylene sulphone and hexamethylphosphoric triamide.

Suitable reaction auxiliaries or acid acceptors for use in the processes (a), (b), (c), (d) and (e) according to the invention are all acid binders which can conventionally be used for such reactions. Preference is given to alkali metal hydroxides such as, for example, sodium hydroxide and potassium hydroxide, alkaline earth metal hydroxides such as, for example, calcium hydroxide, alkali metal carbonates and alkoxides such as sodium carbonate and potassium carbonate, sodium tert-butoxide and potassium tert-butoxide, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethyl-benzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methylpyridine, 1,5-diazabicyclo[4,3,0]-non-5-ene (DBN), 1,8-diazabicyclo-[5,4,0]-undec-7-ene (DBU) and 1,4-diazabicyclo-[2,2,2]-octane (DABCO).

The reaction temperatures in the processes (a), (b), (c), (d) and (e) according to the invention can be varied within a relatively wide range. In general, the processes are carried out at temperatures between −20° C. and +150° C., preferably at temperatures between 0° C. and +100° C.

The processes (a), (b), (c), (d) and (e) according to the invention are generally carried out under atmospheric pressure. However, it is also possible to operate under elevated or reduced pressure.

For carrying out the processes (a), (b), (c), (d) and (e) according to the invention, the starting materials which are required in each case are generally employed in approximately equimolar amounts. However, it is also possible to employ a relatively large excess of one of the components used in each case. The reactions are generally carried out in a suitable diluent in the presence of an acid acceptor, and the reaction mixture is stirred for a number of hours at the respective temperature required. Work-up in the processes (a), (b), (c), (d) and (e) according to the invention is in each case carried out by customary methods (cf. the Preparation Examples).

If required, salts can be prepared from the compounds of the general formula (I) according to the invention. Such salts are obtained in a simple manner by customary salt formation methods, for example by dissolving or dispersing a compound of the formula (I) in a suitable solvent, such as, for example, methylene chloride, acetone, tert-butyl methyl ether or toluene, and adding a suitable base. The salts can then be isolated—if appropriate after prolonged stirring—by concentration or filtration with suction.

The active compounds according to the invention can be used as defoliants, desiccants, haulm killers and, especially, as weed-killers. By weeds in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and railway tracks, and on paths and squares with or without tree plantings. Equally, the compounds can be employed for the control of weeds in perennial crops for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective control of weeds in annual cultures.

The compounds of the formula (I) according to the invention are suitable in particular for the selective control of monocotyledonous and dicotyledonous weeds in monocotyledonous crops, both pre-emergence and post-emergence.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If the extender used is water, it is also possible to employ for example organic solvents as auxiliary solvents. Suitable liquid solvents are essentially the following: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 per cent by weight of active compound, preferably between 0.5 and 90%.

For the control of weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, asulam, atrazine, azimsulfuron, benazolin, benfuresate, bensulfuron(-methyl), bentazon, benzofenap, benzoylprop(-ethyl), bialaphos, bifenox, bromobutide, bromofenoxim, bromoxynil, butachlor, butylate, cafenstrole, carbetamide, chlomethoxyfen, chloramben, chloridazon, chlorimuron(-ethyl), chlornitrofen, chlorsulfuron, chlortoluron, cinmethylin, cinosulfuron, clethodim, clodinafop(-propargyl), clomazone, clopyralid, clopyrasulfuron, cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), difenzoquat, diflufenican, dimefuron, dimepiperate, dimethachlor, dimethametryn, dimethenamid, dinitramine, diphenamid, diquat, dithiopyr, diuron, dymron, EPTC, esprocarb, ethalfluralin, ethametsulfuron(-methyl), ethofumesate, ethoxyfen, etobenzanid, fenoxaprop(-ethyl), flamprop(-isopropyl), flamprop(-isopropyl-L), flamprop(-methyl), flazasulfuron, fluazifop(-butyl), flumetsulam, flumiclorac(-pentyl), flumioxazin, flumipropyn, fluometuron, fluorochloridone, fluoroglycofen(-ethyl), flupoxam, flupropacil, flurenol, fluridone, fluroxypyr, flurprimidol, flurtamone, fomesafen, glufosinate(-ammonium), glyphosate(-isopropylammonium), halosafen, haloxyfop(-ethoxyethyl), hexazinone, imazamethabenz(-methyl), imazamethapyr, imazamox, imazapyr, imazaquin, imazethapyr, imazosulfuron, ioxynil, isopropalin, isoproturon, isoxaben, isoxaflutole, isoxapyrifop, lactofen, lenacil, linuron, MCPA, MCPP, mefenacet, metamitron, metazachlor, methabenzthiazuron, metobenzuron, metobromuron, metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiazon, oxyfluorfen, paraquat, pendimethalin, phenmedipham, piperophos, pretilachlor, primisulfuron(-methyl), prometryn, propachlor, propanil, propaquizafop, propyzamide, prosulfocarb, prosulfuron, pyrazolate, pyrazosulfuron(-ethyl), pyrazoxyfen, pyributicarb, pyridate, pyrithiobac(-sodium), quinchlorac, quinmerac, quizalofop(-ethyl), quizalofop(-p-tefuryl), rimsulfuron, sethoxydim, simazine, simetryn, sulcotrione, sulfentrazone, sulfometuron(-methyl), sulfosate, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the examples below.

PREPARATION EXAMPLES

Example 1

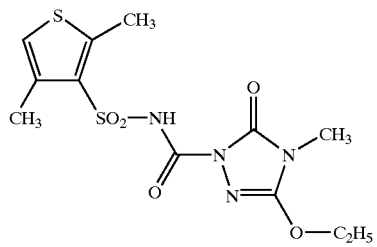

(Process (a))

1.3 g (6.8 mmol) of 2,4-dimethyl-thiophene-3-sulphonamide and 1.1 g (7 mmol) of 1,8-diazabicyclo-[5,4,0]-undec-7-ene (DBU) are added successively to a solution of 1.6 g (6.4 mmol) of 5-ethoxy-4-methyl-2-phenoxycarbonyl-2,4-dihydro-3H-1,2,4-triazol-3-one in 30 ml of acetonitrile. The reaction mixture is stirred at room temperature (about 20° C.) for approximately 15 hours and subsequently concentrated under waterpump vacuum. The residue is then taken up in methylene chloride and washed with 1N hydrochloric acid and then with water. The organic phase is dried with magnesium sulphate and filtered. The filtrate is concentrated under waterpump vacuum and the residue is recrystallized from isopropanol.

This gives 1.1 g (50% of theory) of 5-ethoxy-4-methyl-2-(2,4-dimethyl-thien-3-yl-sulphonylaminocarbonyl)-2,4-dihydro-3H-1,2,4-triazol-3-one of melting point 158° C.

Example 2

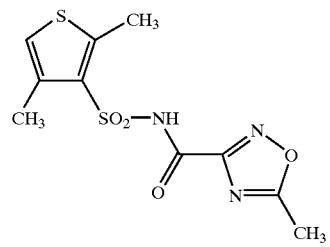

(Process (d))

At 20° C. to at most 35° C., 2.0 g (36 mmol) of potassium hydroxide powder are added to a solution of 1.52 g (12.0 mmol) of 5-methyl-1,2,4-oxadiazol-3-carboxamide in 150 ml of dioxane. After 30 minutes, approximately 50 ml of dioxane are distilled off at from 30° C. to 35° C. under waterpump vacuum. The mixture is subsequently admixed a little at a time with 2.65 g (12.6 mmol) of 2,4-dimethylthiophene-3-sulphonyl chloride and the reaction mixture is stirred at room temperature (about 20° C.) for approximately 12 hours. The mixture is subsequently concentrated under waterpump vacuum and the residue is taken up in water and acidified with 2N hydrochloric acid. The mixture is then extracted twice with 100 ml of methylene chloride each time. The combined organic solutions are washed with water, dried with magnesium sulphate and filtered. The filtrate is concentrated under waterpump vacuum and the residue is recrystallized from ethanol.

This gives 0.7 g (19% of theory) of N-(2,4-dimethyl-thien-3-yl-sulphonyl)-5-methyl-1,2,4-oxadiazol-3-carboxamide of melting point 164° C.

By the methods of Examples 1 and 2, and in accordance with the general description of the preparation processes according to the invention, it is also possible to prepare, for example, the compounds of the formula (I) listed in Table 1 below.

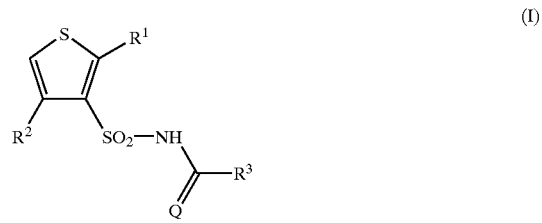

TABLE 1

Examples of compounds of the formula (I)

| Ex. No. | Q | R¹ | R² | R³ | Melting point (° C.) |
|---|---|---|---|---|---|
| 3 | O | CH₃ | CH₃ | 1,4-dimethyl-5-ethyl-1,2,4-triazol-3(2H)-one-yl | 152 |
| 4 | O | CH₃ | CH₃ | 1,4-dimethyl-5-(SCH₃)-1,2,4-triazol-3(2H)-one-yl | 179 |
| 5 | O | CH₃ | CH₃ | 1,4-dimethyl-5-(OC₃H₇-n)-1,2,4-triazol-3(2H)-one-yl | 120 |
| 6 | O | CH₃ | CH₃ | 1,4-dimethyl-5-(OC₃H₇-i)-1,2,4-triazol-3(2H)-one-yl | 137 |
| 7 | O | CH₃ | CH₃ | 1-methyl-4-ethyl-5-(OCH₃)-1,2,4-triazol-3(2H)-one-yl | 122 |
| 8 | O | CH₃ | CH₃ | 1-methyl-4-(OC₂H₅)-5-ethyl-1,2,4-triazol-3(2H)-one-yl | 107 |
| 9 | O | CH₃ | CH₃ | 1,4-dimethyl-5-(C₃H₇-i)-1,2,4-triazol-3(2H)-one-yl | 63 |
| 10 | O | CH₃ | CH₃ | 1,4-dimethyl-5-(SC₂H₅)-1,2,4-triazol-3(2H)-one-yl | 130 |
| 11 | O | CH₃ | CH₃ | 1,4-dimethyl-5-(OCH₃)-1,2,4-triazol-3(2H)-one-yl | 96 |
| 12 | O | CH₃ | CH₃ | 1-methyl-4-cyclopropyl-5-(OC₂H₅)-1,2,4-triazol-3(2H)-one-yl | 82 |
| 13 | O | CH₃ | CH₃ | 1-methyl-4-ethyl-5-(OC₂H₅)-1,2,4-triazol-3(2H)-one-yl | 129 |
| 14 | O | CH₃ | CH₃ | 1,4-dimethyl-5-(S-CH₂-C≡CH)-1,2,4-triazol-3(2H)-one-yl | 117 |
| 15 | O | CH₃ | CH₃ | 1-methyl-4-cyclopropyl-5-(OCH₃)-1,2,4-triazol-3(2H)-one-yl | 159 |
| 16 | S | CH₃ | CH₃ | 1,4-dimethyl-5-(OC₂H₅)-1,2,4-triazol-3(2H)-one-yl | 124 |
| 17 | O | CH₃ | CH₃ | 1-methyl-4-cyclopropyl-5-(CH₂OCH₃)-1,2,4-triazol-3(2H)-one-yl | 91 |

TABLE 1-continued

Examples of compounds of the formula (I)

| Ex. No. | Q | R¹ | R² | R³ | Melting point (° C.) |
|---|---|---|---|---|---|
| 18 | O | CH₃ | CH₃ | 1-methyl-4-cyclopropyl-5-(i-C₃H₇O)-1,2,4-triazol-3(4H)-one | 128 |
| 19 | O | CH₃ | CH₃ | 1,4,5-trimethyl-1,2,4-triazol-3(4H)-one | 70 |
| 20 | O | CH₃ | CH₃ | 1,4-dimethyl-5-(CH₂OCH₃)-1,2,4-triazol-3(4H)-one | 55 |
| 21 | O | CH₃ | CH₃ | 1-methyl-4-cyclopropyl-5-(n-C₃H₇O)-1,2,4-triazol-3(4H)-one | 114 |
| 22 | O | CH₃ | CH₃ | 1-methyl-4-cyclopropyl-5-cyclopropyl-1,2,4-triazol-3(4H)-one | 163 |
| 23 | O | CH₃ | CH₃ | 1-methyl-4-(i-C₃H₇)-5-cyclopropyl-1,2,4-triazol-3(4H)-one | 95 |
| 24 | O | CH₃ | CH₃ | 1,4-dimethyl-5-Br-1,2,4-triazol-3(4H)-one | 129 |
| 25 | O | CH₃ | CH₃ | 1,4-dimethyl-5-(OCH₂CF₃)-1,2,4-triazol-3(4H)-one | 177 |
| 26 | O | CH₃ | CH₃ | 1-methyl-4-cyclopropyl-5-Br-1,2,4-triazol-3(4H)-one | 165 |
| 27 | O | CH₃ | CH₃ | 1,4-dimethyl-5-(n-C₃H₇)-1,2,4-triazol-3(4H)-one | 160 |
| 28 | O | CH₃ | CH₃ | 1-methyl-4-cyclopropyl-5-(i-C₄H₉)-1,2,4-triazol-3(4H)-one | 62 |
| 29 | O | CH₃ | CH₃ | 1-methyl-4-cyclopropyl-5-CH₃-1,2,4-triazol-3(4H)-one | 164 |
| 30 | O | CH₃ | CH₃ | 1-methyl-4-cyclopropyl-5-C₂H₅-1,2,4-triazol-3(4H)-one | 125 |
| 31 | O | CH₃ | CH₃ | 1-methyl-4-C₂H₅-5-CH₃-1,2,4-triazol-3(4H)-one | 74 |

TABLE 1-continued

Examples of compounds of the formula (I)

| Ex. No. | Q | R¹ | R² | R³ | Melting point (° C.) |
|---|---|---|---|---|---|
| 32 | O | CH₃ | CH₃ | 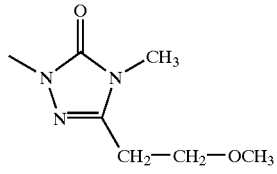 | 158 |
| 33 | S | CH₃ | CH₃ | 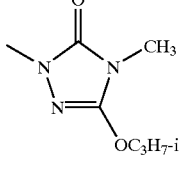 | 112 |
| 34 | S | CH₃ | CH₃ | 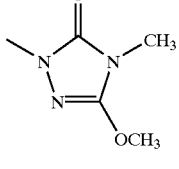 | 147 |
| 35 | S | CH₃ | CH₃ | 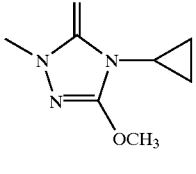 | 139 |
| 36 | S | CH₃ | CH₃ | 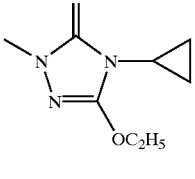 | 136 |
| 37 | S | CH₃ | CH₃ | 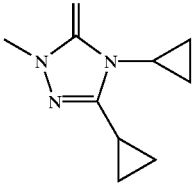 | 78 |
| 38 | S | CH₃ | CH₃ | 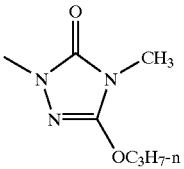 | 97 |
| 39 | O | CH₃ | CH₃ | 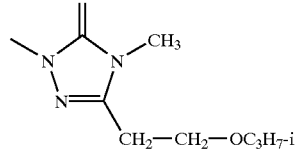 | 66 |
| 40 | O | CH₃ | OCH₃ | 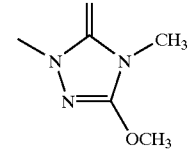 | |
| 41 | O | CH₃ | OCH₃ | 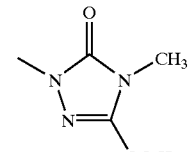 | |
| 42 | O | CH₃ | OCH₃ | 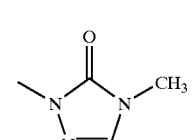 | |
| 43 | O | CH₃ | OCH₃ | 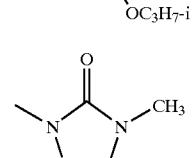 | |

Starting Materials of the Formula (II):

Example (II-1)

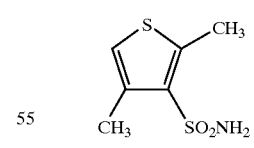

A mixture of 6.0 g (29 mmol) of 2,4-dimethyl-thiophene-3-sulphonyl chloride and 30 ml of 25% strength aqueous ammonia solution is stirred at room temperature (about 20° C.) for 12 hours. The resulting crystalline product is then isolated by filtration with suction.

This gives 4.3 g (80% of theory) of 2,4-dimethyl-thiophene-3-sulphonamide of melting point 135° C.

Starting Materials of the Formula (IV):

Example (IV-1)

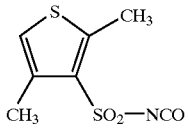

A mixture of 19.1 g (100 mmol) of 2,4-dimethyl-thiophene-3-sulphonamide, 10.0 g (100 mmol) of butyl isocyanate and 100 ml of chloroform is heated to the boil, and phosgene is introduced into the mixture at reflux temperature for 4 hours. The mixture is subsequently concentrated under waterpump vacuum and the residue is subjected to distillation under oilpump vacuum.

This gives 10.3 g (47% of theory) of 2,4-dimethyl-thien-3-yl-sulphonyl isocyanate of a boiling range of from 135° C. to 140° C. (at 1 mbar).

Starting Materials of the Formula (VI):

Example (VI-1)

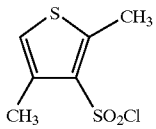

A solution of 13.9 g (109 mmol) of 3-amino-2,4-dimethyl-thiophene in 30 ml of 10% strength hydrochloric acid is cooled to 0° C. and admixed with 50 ml of conc. hydrochloric acid. With cooling to from 0° C. to –5° C., a solution of 8.6 g (125 mmol) of sodium nitrite in 22 ml of water is then added dropwise with stirring. The reaction mixture is stirred at from 0° C. to –5° C. for approximately one hour. Excess sodium nitrite is subsequently destroyed using amidosulphonic acid. The resulting diazonium salt solution is added dropwise, at about 15° C., to a solution of 12 g of sulphur dioxide in 100 ml of 1,2-dichloro-ethane. 600 mg of copper(I) chloride and 600 mg of dodecyl-trimethylammonium bromide are then added and the reaction mixture is stirred at about 40° C. for approximately one hour and at room temperature (about 20° C.) for a further 12 hours. After addition of 6 g of 30% strength hydrogen peroxide solution, the mixture is stirred for a further 30 minutes. The organic phase is then separated off, washed twice with water, dried with magnesium sulphate and filtered. The filtrate is concentrated under waterpump vacuum, the residue is digested with petroleum ether and the resulting crystalline product is isolated by filtration with suction.

This gives 9.6 g (42% of theory) of 2,4-dimethyl-thiophene-3-sulphonyl chloride of melting point 79° C.

In each case by the methods of Examples (II-1), (IV-1) and (VI-1) it is also possible to prepare, for example, the compounds of the formulae (II), (IV) and (VI) listed in Table 2 below:

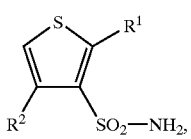

(II)

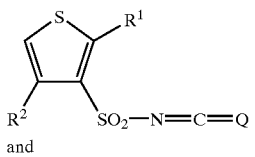

(IV)

and

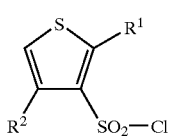

(VI)

TABLE 2

Examples of the compounds of the formulae (II), (IV) and (VI) [i.e. the radicals $R^1$ and $R^2$ apply to each of these 3 formulae]; Q is O or S.

| Example No. II- IV- VI- | $R^1$ | $R^2$ |
|---|---|---|
| 2 | $CH_3$ | $C_2H_5$ |
| 3 | $CH_3$ | $C_3H_7$-n |
| 4 | $CH_3$ | $C_3H_7$-i |
| 5 | $CH_3$ | $CF_3$ |
| 6 | $CH_3$ | Cl |
| 7 | $CH_3$ | $OCH_3$ |
| 8 | $CH_3$ | $OC_2H_5$ |
| 9 | $CH_3$ | $OC_3H_7$-n |
| 10 | $CH_3$ | $OC_3H7$-i |
| 11 | $C_2H_5$ | $CH_3$ |
| 12 | $C_3H_7$-n | $CH_3$ |
| 13 | $C_3H_7$-i | $CH_3$ |

USE EXAMPLES

Example A

Pre-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is watered with the preparation of the active compound. Advantageously, the amount of water per unit area is kept constant. The active compound concentration in the preparation is not important, only the active compound application rate per unit area is critical.

After three weeks, the degree of damage to the plants is rated in % damage in comparison with the development of the untreated control.

The figures denote:

0%=no effect (like untreated control)

100%=total destruction

In this test, for example, the compounds of Preparation Example 1, 3, 4, 5, 11 and 12 exhibit very strong activity against weeds, and some of them are tolerated well by crop plants, such as, for example, maize and wheat (cf. Table A).

"ai." (active ingredient)=active compound

TABLE A

Pre-emergence test/greenhouse

| Active compound of Preparation Example No. | Application rate (g of ai./ha) | Maize | Bromus | Cyperus | Lolium | Setaria | Chenopodium | Matricaria | Solanum |
|---|---|---|---|---|---|---|---|---|---|
| (3) [structure: thiophene with 2,4-dimethyl, sulfonyl carboxamide linked to triazolinone with 4-methyl, 3-ethyl] | 125 | 5 | 100 | 100 | 100 | 100 | 100 | 100 | 100 |

| Active compound of Preparation Example No. | Application rate (g of ai./ha) | Wheat | Bromus | Cyperus | Lolium | Setaria | Chenopodium | Matricaria | Solanum |
|---|---|---|---|---|---|---|---|---|---|
| (1) [structure: thiophene with 2,4-dimethyl, sulfonyl carboxamide linked to triazolinone with 4-methyl, 3-ethoxy] | 125 | 0 | 100 | 95 | 100 | 100 | 100 | 100 | 100 |

| Active compound of Preparation Example No. | Application rate (g of ai./ha) | Wheat | Maize | Bromus | Cyperus | Lolium | Setaria | Chenopodium | Matricaria | Solanum |
|---|---|---|---|---|---|---|---|---|---|---|
| (4) [structure: thiophene with 2,4-dimethyl, sulfonyl carboxamide linked to triazolinone with 4-methyl, 3-methylthio] | 125 | 0 | 0 | 95 | 95 | 100 | 100 | 90 | 90 | 80 |

| Active compound of Preparation Example No. | Application rate (g of ai./ha) | Bromus | Cyperus | Lolium | Setaria | Chenopodium | Matricaria | Solanum |
|---|---|---|---|---|---|---|---|---|

TABLE A-continued

Pre-emergence test/greenhouse

| Active compound of Preparation Example No. | Application rate (g of ai./ha) | Alope-curus | Amaran-thus Abutilon | | Sinapis | Xanthium |
|---|---|---|---|---|---|---|
| (11) | 125 | 100 | 100 | 100 100 95 | 100 | 95 |
| (5) | 250 | 70 | 90 | 90 | 95 | 90 |
| (12) | 250 | 70 | 90 | 90 | 95 | — |

"ai." (active ingredient) = active compound

Example B
Post-Emergence Test

Solvent: 5 parts by weight of acetone
Emulsifier: 1 part by weight of alkylaryl polyglycol ether
To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the amounts of active compound desired in each case are applied in 1000 l of water/ha.

After three weeks, the degree of damage to the plants is rated in % damage in comparison with the development of the untreated control.

The figures denote:

0%=no effect (like untreated control)

100% =total destruction

In this test, for example, the compounds of Preparation Examples 6, 13 and 14 exhibit very strong activity against weeds, and some of them are tolerated well by crop plants, such as, for example, maize (cf. Table B).

What is claimed is:

1. A compound of the Formula (XX)

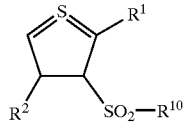

(XX)

wherein

R$^1$ is selected from the group consisting of cyano; halogen; alkyl, alkenyl, alkinyl, alkoxy, alkenyloxy or alki-

TABLE B

| Active compound of Preparation Example No. | Application rate (g of ai/ha) | Maize | Setaria | Abutilon | Amaranthus | Sinapis |
|---|---|---|---|---|---|---|
| (6) | 250 | 10 | 80 | — | 90 | 100 |
| (13) | 250 | — | 80 | 80 | 100 | 100 |
| (14) | 250 | 10 | 90 | — | 95 | 95 |

Post-emergence test/greenhouse nyloxy having in each case up to 6 carbon atoms; and cyano-, halogen- or $C_1$–$C_4$-alkoxy-substituted alkyl, alkenyl, alkinyl, alkoxy, alkenyloxy or alkinyloxy having in each case up to 6 carbon atoms;

$R^2$ is selected from the group consisting of cyano; halogen; alkyl, alkenyl, alkinyl, alkoxy, alkenyloxy or alkinyloxy having in each case up to 6 carbon atoms; and cyano-, halogen- or $C_1$–$C_4$-alkoxy-substituted alkyl, alkenyl, alkinyl, alkoxy, alkenyloxy or alkinyloxy having in each case up to 6 carbon atoms; and $R^{10}$ is —$NH_2$.

2. The compound of claim 1, wherein $R^1$ is selected from the group consisting of cyano; halogen; $C_1$–$C_4$-alkyl; $C_2$–$C_4$-alkenyl; $C_2$–$C_4$-alkinyl; $C_1$–$C_4$-alkoxy; $C_2$–$C_4$-alkenyloxy; $C_2$–$C_4$-alkinyloxy; cyano-, halogen- or $C_1$–$C_4$-alkoxy-substituted $C_1$–$C_4$-alkyl; cyano- or halogen-substituted $C_2$–$C_4$-alkenyl or $C_2$–$C_4$-alkinyl; cyano-, halogen- or $C_1$–$C_4$-alkoxy-substituted $C_1$–$C_4$-alkoxy; and cyano- or halogen-substituted $C_2$–$C_4$-alkenyloxy or $C_2$–$C_4$-alkinyloxy; and $R^2$ is selected from the group consisting of cyano; halogen; $C_1$–$C_4$-alkyl; $C_2$–$C_4$-alkenyl; $C_2$–$C_4$-alkinyl; $C_1$–$C_4$-alkoxy; $C_2$–$C_4$-alkenyloxy; $C_2$–$C_4$-alkinyloxy; cyano-, halogen- or $C_1$–$C_4$-alkoxy-substituted $C_1$–$C_4$-alkyl; cyano- or halogen-substituted $C_2$–$C_4$-alkenyl or $C_2$–$C_4$-alkinyl; cyano-, halogen- or $C_1$–$C_4$-alkoxy-substituted $C_1$–$C_4$-alkoxy; and cyano- or halogen-substituted $C_2$–$C_4$-alkenyloxy or $C_2$–$C_4$-alkinyloxy.

3. The compound of claim 2, wherein $R^1$ and $R^2$ are both methyl.

* * * * *

UNITED STATES PATENT AND TRADEMARK OFFICE
CERTIFICATE OF CORRECTION

PATENT NO. : 6,566,536 B2
DATED : May 20, 2003
INVENTOR(S) : Klaus-Helmut Muller et al.

It is certified that error appears in the above-identified patent and that said Letters Patent is hereby corrected as shown below:

Column 30,
Lines 3-10, Formula (XX) should read as follows:

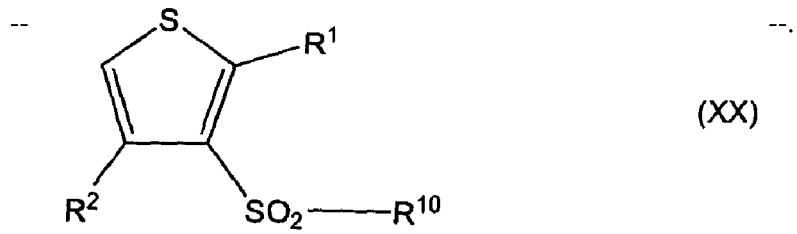

Signed and Sealed this

First Day of November, 2005

JON W. DUDAS
*Director of the United States Patent and Trademark Office*